United States Patent [19]

Braid

[11] 4,305,832
[45] Dec. 15, 1981

[54] LUBRICANT STABILIZERS

[75] Inventor: Milton Braid, Westmont, N.J.

[73] Assignee: Mobil Oil Corporation, New York, N.Y.

[21] Appl. No.: 102,098

[22] Filed: Dec. 10, 1979

[51] Int. Cl.$^3$ .................... C10M 3/36; C07C 149/36; C07C 149/32

[52] U.S. Cl. .................... 252/48.2; 568/23; 568/48; 568/49

[58] Field of Search .............. 260/608, 609 F; 568/23, 568/48, 49; 252/48.2, 404

[56] References Cited

U.S. PATENT DOCUMENTS

| | | | |
|---|---|---|---|
| 2,306,354 | 12/1942 | Cook et al. | 252/48.2 |
| 2,831,030 | 4/1958 | Chenicek | 252/48.2 |
| 3,067,259 | 12/1962 | Bailey | 260/609 F |
| 3,497,181 | 2/1970 | Braid | 568/592 |
| 3,634,521 | 1/1972 | Clark et al. | 260/609 F |
| 3,683,032 | 8/1972 | Braid | 568/592 |

FOREIGN PATENT DOCUMENTS 49-102654  9/1974  Japan ..................... 568/48

*Primary Examiner*—Donald G. Daus
*Assistant Examiner*—Diana G. Rivers
*Attorney, Agent, or Firm*—Charles A. Huggett; Michael G. Gilman; James D. Tierney

[57] ABSTRACT

Phenol sulfides, disulfides, polysulfides and oligomers thereof when reacted with alkyl vinyl ethers provide addition products substantially comprised of novel acetal derivatives which are effective oxidation inhibitors when incorporated into organic media normally susceptible to oxidative degradation.

30 Claims, No Drawings

LUBRICANT STABILIZERS

BACKGROUND OF THE INVENTION

1. Field of the Invention

This invention is directed to the discovery that sulfided phenols, i.e., phenol sulfides, disulfides, polysulfides and oligomers thereof as well as mixtures of the foregoing form addition products with alkyl vinyl ethers which are excellent oxidation inhibitors when incorporated into organic media which is normally subject to oxidative degradation. This invention is more particularly directed to hydrocarbyl compositions comprising lubricants or greases thereof which exhibit improved oxidation inhibition when the above-described addition derivatives are added thereto. This application is further directed to novel compounds consisting of said derivatives. Included within this class of novel compounds are acetal derivatives of phenol sulfides.

Description of the Prior Art

Mixed acetals of phenols and naphthols have been previously disclosed. For example, U.S. Pat. Nos. 3,497,181 and 3,683,032 disclose aryloxy (alkyloxy) alkanes as additives useful for inhibiting the oxidative deterioration of organic substrates normally susceptible to such degradation. Also, 2,2'-thiobis(alkylphenols) and 2,2'-dithiobis(alkylphenols) are known antioxidant additives. However, the present invention directed to derivatives of phenolic thioethers and polythioethers and compositions containing same have not been previously disclosed by any references known to applicant.

SUMMARY OF THE INVENTION

In accordance with the invention sulfided phenols and oligomers thereof as well as mixtures containing same can be partially or completely converted to addition product derivatives. These addition products are derived from sulfurized phenols of the general structure:

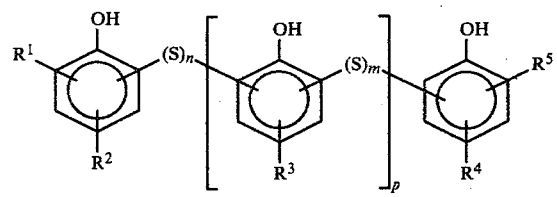

wherein $R^1$ and $R^5$ are hydrogen or alkyl groups having from 1 to about 16 carbon atoms in any isomeric structural arrangement, $R^1$ and $R^5$ may be the same or different; $R^2$, $R^3$, and $R^4$ are hydrogen or an alkyl group having from 1 to about 18 carbon atoms in any isomeric structural arrangement $R^2$, $R^3$ and $R^4$ may be the same or different except that the total number of carbon atoms cannot be less than 4 if at least one of these substituent groups is hydrogen; n and m are 1 to 4 and may be the same or different, and p is 1 to 4 or zero. The sulfide, disulfide or polysulfide bridges may be sited at any ring positions, but positions ortho to the hydroxyl groups are preferred.

The addition products of this invention are predominantly acetals resulting from Markovnikov addition of the phenolic hydroxyl groups to alkyl vinyl ethers. All of the available hydroxyl groups may participate in the acetal formation or some may remain unreacted. A single alkyl vinyl ether or two or more different alkyl vinyl ethers may be used sequentially or mixtures of alkyl vinyl ethers may be used to form acetals of the general structures:

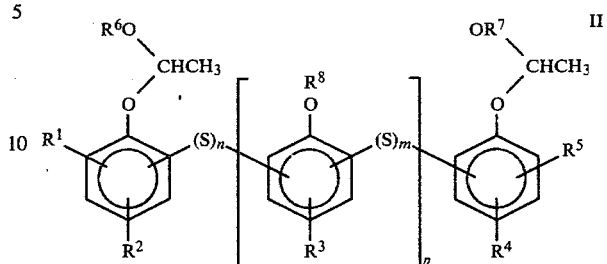

and

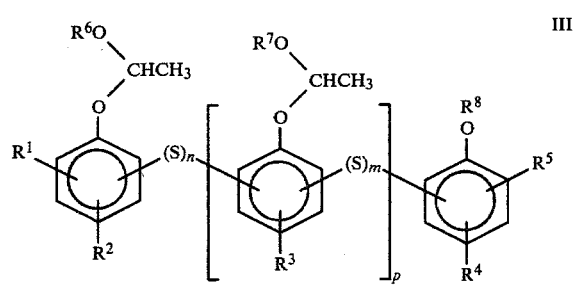

wherein $R^1$, $R^2$, $R^3$, $R^4$, $R^5$, n, m, and p are as defined above, $R^6$ and $R^7$ are alkyl groups having 1 to about 6 carbon atoms and may be the same or different and $R^8$ is hydrogen or an alkoxyalkyl group having from 1 to about 6 carbon atoms.

Anti-Markovnikov addition products of the alkyl vinyl ethers of partial general structure:

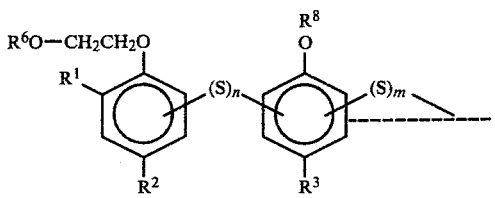

wherein $R^1$, etc. are as defined above. Anti-Markovnikov can also be formed which are mixed alkyl aryl glycol ethers. As for the Markovnikov addition products all or some of the phenolic hydroxyl groups may participate in the addition reaction. Addition products of sulfurized phenols both acetal and glycol ether structures are within the scope of this invention.

The acetal addition products may be separated or mixtures of predominatly acetal and glycol ether products may be used in the lubricant compositions contemplated herein.

It is a distinctive feature of the acetal addition products of this invention that the sulfur atoms present in these structures provide a mode of antioxidation, i.e., hydroperoxide or peroxide decomposition, which is different from the antioxidation provided by the phenolic elements, i.e., chain termination, or the acetal structures. The combination of antioxidation modes in the same antioxidant molecule is uniquely internally synergistic and/or complementary, and functionally enhancing.

It is a further feature of this invention that antioxidant-effective phenol sulfides which have limited utility due to low solubility in lubricating oils and compositions are rendered by partial or complete conversion to the herein described addition products substantially more soluble. The conversions of the phenol sulfides may be carried out by catalytic or non-catalytic additions of the sulfided phenol to alkyl vinyl ethers. The additions may, as hereinbefore described, be carried out in successive steps to different alkyl vinyl ethers or alternatively to a mixture of such ethers. All of the available hydroxyl groups or only some of them may be added to. Accordingly, some free hydroxyl groups can be allowed to remain, but at least one hydroxyl group in each phenol sulfide molecule undergoes addition.

Generally speaking, the phenols (e.g., p-t-octylphenol) in accordance with the present invention are initially reacted with a sulfur halide (e.g., sulfur monochloride), although the phenol sulfides may also be further reacted with other phenols and a sulfur halide, and then the phenol sulfide product is reacted with an alkyl vinyl ether (e.g., ethyl vinyl ether). The reaction may be acid (e.g., acetic) catalyzed. The resulting products may still contain substantial amounts of unreacted hydroxyl groups. These products may then be further reacted (uncatalyzed) with additional alkyl vinyl ether (it may be the same or a different vinyl ether such as butyl vinyl ether), at a higher temperature. Although some still unreacted —OH remains there is virtual total conversion of the reacted alkyl vinyl ether to —OH addition product. Choice of solvent as well as the presence of absence of a catalyst also seems to have an effect upon the degree of conversion as do the reactive temperature and the length of the reaction period. These factors appear to be related to the structures of the reactant phenol sulfides.

The novel compounds disclosed herein may be prepared from any suitable phenol sulfide, disulfide, polysulfide or oligomers thereof. Preferred are 2,2'-thiobis-(alkylphenols) or 2,2'-dithiobis(alkylphenols) and oligomeric 2,2'-thiobis(alkylphenols) and 2,2'-dithiobis(alkylphenols) containing 3 to 4 alkylphenol units and particularly such oligomers containing both sulfide and disulfide groups wherein the alkyl moiety contains from 1 to about 20 carbon atoms. More preferred are alkyl moieties containing from 4 to 12 carbon atoms. Especially preferred are p-t-octyl alkyl groups.

The alkyl vinyl ethers preferred for use herein will generally contain from 1 to about 12 carbon atoms in the alkyl group. Especially preferred are $C_1$–$C_6$ vinyl ethers such as ethyl vinyl ether and butyl vinyl ether.

As previously stated the conversion reaction can be catalyzed or uncatalyzed. Lower monocarboxylic acids, i.e., from $C_1$ to about $C_4$, such as acetic acid have proven to be suitable catalysts. Also such acids as p-toluenesulfonic and trifluoromethanesulfonic have also proven useful. However, useful catalysts are not limited thereto. Any suitable catalyst known in the art may also be used. The reaction may also take place in the presence of a suitable solvent. Non-exhaustive suitable solvents include such materials as benzene, toluene and xylene.

Reaction conditions may vary from a temperature of about 20° C. to 150° C. Molar ratios of reactants will generally be from 0.25 to 10:1 of alkyl vinyl ether to reactive hydroxyl groups. Preferred is 0.4 to 4:1 and most preferred is 0.5 to 2:1 moles of alkyl vinyl ether to each mole of reactive hydroxyl. Usually the reaction will be carried out at atmospheric pressure, however, higher pressures may be used if so desired. Reaction times may vary from about 0.25 hr. to about 12 hrs. Suitable reaction times are from about 0.5 hr. to about 6 hrs. with from about 1 hr. to about 4 hrs. being most suitable.

The additive compounds of this invention or mixtures thereof may be used in mineral oils, synthetic oils or mixtures of mineral or refined petroleum and synthetic oils of lubricating viscosity. Generally, from about 0.1 to about 5 wt. % of the total composition will be effective for the intended purpose. The lubricant compositions, greases and various functional fluids, such as hydraulic fluids, brake fluids, transmission fluids, heat-transfer fluids containing the additive compounds in accordance with the invention may also contain other known additives for their intended purposes in amounts of up to 10–20 wt. %.

DESCRIPTION OF SPECIFIC EMBODIMENTS

Having generally described the invention the following specific material and examples are exemplary of the invention and no limitations, express or otherwise, are intended thereby.

EXAMPLE 1

A typical solvent refined mineral oil base stock having a viscosity of 130 SUS at 100° F.

EXAMPLE 2

DBPC (2,6-di-tertiary-butyl-4-methylphenol or 2,6-di-t-butyl-p-cresol) obtained commercially.

EXAMPLE 3

Preparation of
2,2'-thiobis-(4-tert-butyl-6-methylphenol) containing elemental sulfur To a solution of 4-tert-butyl-2-methylphenol (82.2 g; 0.5 mole) in petroleum ether (200 ml.) cooled at 8° C. there was added over about 5 hr. sulfur monochloride (33.7 g; 0.25 mole). The temperature was maintained at 6°–8° C. throughout the addition period; an ice bath was provided during a subsequent 20 hr. reaction period. The reaction mixture was then treated with diluted ammonium hydroxide solution and the resulting mixture was extracted with benzene. After solvent stripping of the dried extract, there was obtained 93 g. of reddish oil reaction product for which the infrared spectrum matched that of an authentic sample of 2,2'-thiobis-(4-tert-butyl-6-methylphenol) and the gas chromatogram showed only a single major product peak with an elution time identical to the authentic thiobisphenol. Elemental analysis matched that of the 2,2'-thiobis(alkylphenol), $C_{22}H_{30}O_2S_2$, rather than the 2,2'-thiobis(alkylphenol), $C_{22}H_{30}O_2S$ indicating the presence of elemental sulfur. The sulfur could be completely removed by percolating through neutral alumina.

Anal. Calc'd for $C_{22}H_{30}O_2S$: C,73.70; H,8.43; S,8.94; Cl,0. Calc'd for $C_{22}H_{30}O_2S_2$: C,67.65; H,7.74; S,16.42; Cl,0. Found: C,67.66; H,7.92; S,15.0; Cl,0.1.

EXAMPLE 4

Addition of 2,2'-thiobis (4-tert-butyl-6-methylphenol) to butyl vinyl ether

To a solution of 2,2'-thiobis-(4-tert-butyl-6-methylphenol) (17.5 g) in benzene (200 ml.) containing one drop of acetic acid refluxing at 76° C. there was added during 0.75 hr. a solution of butyl vinyl ether (40 g) in petroleum ether (50 ml). The reaction mixture was then refluxed at 76° C. for an additional 2 hr. and then worked up by washing with water, aqueous sodium bicarbonate solution and again with water. The dried organic portion was stripped by rotary film distillation at reduced pressure leaving the acetal addition product as an amber moderately viscous oil. The infrared spectrum of this product showed substantial intensity reduction of absorption band due to hydroxyl, but it was not completely removed.

EXAMPLE 5

2,2'-thiobis-(4-tert-octylphenol) (TBP) is prepared by reaction of 4-tert-octylphenol (p-1,1,3,3-tetramethylbutylphenol prepared by alkylation of phenol with diisobutylene) with sulfur dichloride as described in U.S. Pat. No. 2,971,940.

EXAMPLE 6

Addition of 2,2'-thiobis-(4-tert-octylphenol) to a deficiency of butyl vinyl ether To a refluxing solution of 2,2'-thiobis-(4-tert-octylphenol) (44.3 g) in benzene (200 ml.) containing one drop of glacial acetic acid there was added rapidly butyl vinyl ether (5 g.). The reaction mixture was refluxed for 6 hrs. and then worked up by washing first with water, then aqueous sodium bicarbonate solution, and water. After drying and solvent stripping on a rotary evaporator, the residue was taken up in n-pentane, unreacted 2,2'-thiobis-(4-tert-octylphenol) was filtered off and the filtrate was stripped of solvent leaving the addition product containing acetals as a viscous liquid.

EXAMPLE 7

Complete addition of 2,2'-thiobis-(4-tert-octylphenol) to butyl vinyl ether

To solution of 2,2'-thiobis-(4-tert-octylphenol) (44.3 g) in benzene (200 ml.) heated to 78° C. there was added during 1.75 hr. butyl vinyl ether (50 g) while the temperature was maintained at 82°–85° C. After addition was completed the reaction mixture was heated at 85° C. for a further 3 hr. and then was filtered. The filtrate was stripped of solvent and unreacted butyl vinyl ether leaving a hazy viscous yellow oil (66 g). The oil was filtered through filter aid to give the complete addition product diacetal, a clear viscous yellow oil.

Anal. Calculated for $C_{40}H_{66}O_4S$: C, 74.71; H, 10.34; S, 4.98. Found: C, 74.10; H, 10.08; S, 4.33.

EXAMPLE 8

Addition of 2,2'-thiobis-(4-tert-octylphenol) to ethyl vinyl ether

Following the method of Examle 7, ethyl vinyl ether (50 g) was added to 2,2'-thiobis-(4-tert-octylphenol) (44.3 g) in benzene at temperatures of 75°–78° C. for addition and reaction. The acetal addition product was a brown viscous oil. The infrared spectrum showed that addition was incomplete and phenolic hydroxyl groups were still present in significant amounts. This was supported by elemental analysis.

Anal. Calculated for comlete acetal addition, $C_{36}H_{58}O_4S$: C, 73.67; H, 9.96. Found: C, 71.50; H, 9.47.

EXAMPLE 9

Preparation mixed 2-tert-butyl-4-methyl/p-cresol sulfurized phenol

To a solution of 2-tert-butyl-4-methylphenol (65.7 g) and p-cresol (21.6 g) in n-octane (150 ml) heated at 125° C. [a solution of sulfur monochloride (54 g) in n-octane (50 ml)] was' added over 1.5 hr. After addition was completed the reaction mixture was stirred at 125° C. for about one additional hour and then poured into a mixture of ammonium hydroxide (150 ml) and ice. The resulting organic-aqueous mixture was extracted several times with benzene. The combined extract was washed with water, dried and stripped of solvent by rotary evaporation. The residue, a phenol sulfide comprising an average structure of two o-tert-butyl-p-methylphenol end groups and a center p-cresol with two ortho sulfide-disulfide-polysulfide bridges each with an average of 1.5 sulfur atoms was obtained a viscous dark oil.

Anal. Calculated for $C_{28}H_{33}O_3S_3$: C, 65.46; H, 6.47; S, 18.7. Found: C, 65.60; H, 8.27; S, 17.7.

EXAMPLE 10

Sulfurized 4-tert-octylphenol

To a solution of 4-tert-octylphenol (154.7 g) in n-octane (150 ml.) heated at 125° C. sulfur monochloride (50.6 g) was added over a 5 hr. period while stirring. The temperature was maintained during the addition at 125°–127° C. and for a further 0.25 hr. The reaction mixture was allowed to cool to room temperature, and it was poured while stirring into ammonium hydroxide solution (150 ml). The resulting mixture was extracted with benzene several times. The combined extracts were washed with water and dried. After removal of solvents by rotary film evaporation under reduced pressure the sulfurized phenol was obtained as viscous dark oil containing 14.5% of sulfur. Gas chromatography of the silylated sulfurized phenol indicated that it contained about 60% of disulfide and a small amount of oligomeric phenol sulfides and about 40% of the monosulfide.

EXAMPLE 11

Addition product of sulfurized 4-tert-octylphenol and ethyl vinyl ether

To a solution of sulfurized 4-tert-octylphenol (44.3 g) prepared as in Example 10 in benzene (200 ml.) heated at 80° there was added while stirring during more than 3 hrs. a solution of ethyl vinyl ether (50 g) in benzene (about 125 ml). The rate of addition was slow such that the reaction temperature did not fall below 76°–80° C. After addition was completed the reaction mixture was heated at reflux for 1.5 hr. The reaction mixture was then stripped of solvent and unreacted ethyl vinyl ether by rotary film evaporation at reduced pressure leaving the acetal containing addition product (55.2 g) as slightly hazy viscous oil. The oil was taken up in n-pentane, refiltered to remove 0.3 g of solids and stripped of solvent to leave the addition product.

EXAMPLE 12

Butyl vinyl ether addition product of sulfurized phenol from mixed 2-tert-butyl-4-methylphenol and p-cresol To a solution of the sulfurized phenol prepared from a mixture of 2-tert-butyl-4-methylphenol and p-cresol as described in Example 9 (32 g) in benzene (250 ml.) heated to 84° C. there was added during 1 hr. while stirring butyl vinyl ether (50 g). Heating and stirring of the mixture at 84° C. was continued for 2.5 hrs. and then solvent and unreacted butyl vinyl ether were removed by rotary film evaporation under reduced pressure. The addition product was obtained as a dark viscous oil which still contained unreacted hydroxyl groups as well as acetal as shown by the infrared spectrum.

EXAMPLE 13

Preparation of mixed 4-tert-butyl-2-methylphenol/p-cresol sulfurized phenol

By the method of Example 9 an isomeric mixed phenol sulfide was prepared using 4-tert-butyl-2-methylphenol (65.7 g), p-cresol (21.6 g) and sulfur monochloride (54 g) in n-octane solvent at 125° C. The sulfurized phenol was obtained as a dark viscous oil containing 18.2% of sulfur. Theory for the nominal structure in which ortho sulfur bridges connect a central p-cresol with two p-tert-butyl-o-methylphenol end groups and each sulfur bridge has an average value of 1.5 is 18.7% sulfur.

EXAMPLE 14

Butyl vinyl ether addition product of the sulfurized phenol prepared from a mixture of 4-tert-butyl-2-methylphenol and p-cresol To a solution of the sulfurized phenol made from a mixture of 4-tert-butyl-2-methylphenol and p-cresol as described in Example 12 (40 g) in benzene (250 ml.) heated at 84° C. there was added during 0.75 hr. while stirring butyl vinyl ether (50 g). Heating and stirring were continued at 84° C. for 4 hrs. more after addition had been completed. The residue after stripping of solvent and unreacted butyl vinyl ether completely, showed substantial unreacted hydroxyl in the infrared spectrum. It was taken up in xylene (75 ml) and treated with butyl vinyl ether (50 g) at 108° C. for 4.25 hrs. After solvent and butyl vinyl ether were removed by rotary evaporation under reduced pressure, the addition product containing acetals and minor amounts of phenolic hydroxyl (as shown by infrared spectrum) was obtained as a viscous brown oil (54 g).

EXAMPLE 15

Ethyl vinyl ether and butyl vinyl ether sequential addition products of 2,2-thiobis-(4-tert-octylphenol)

Following the method of Example 4, 2,2'-thiobis-(4-tert-octylphenol) (44.3 g) and ethyl vinyl ether were reacted in benzene using acetic acid as catalyst at 76°-80° C. After reaction and removal of benzene and unreacted ethyl vinyl ether, the product still contained a substantial amount of unreacted phenolic hydroxyl groups (infrared spectrum). This product was taken up in benzene heated at 80° C. and butyl vinyl ether (5 g) was added during 0.5 hr. Heating at 80° C. was continued for 2.25 hrs. and the reaction was worked up as in Example 4. The mixed ethyl vinyl ether-butyl vinyl ether acetal addition product was obtained as a dark viscous oil.

Certain of the examples were then subjected to a Catalytic Oxidation Test described hereinbelow after being incorporated into the above-referred to base oil (Example 1). For purposes of comparison unconverted phenol sulfides were also similarly tested. The test data contained in the Table below in which the greatest weight is given to the viscosity change, ΔKV, clearly demonstrate the excellent antioxidant characteristics of the additives disclosed herein. It is moreover clearly apparent from the test data that these additives are superior to widely used 2,6-di-tert-butyl-4-methylphenol, which is representative of the hindered phenol class of excellent antioxidants, and it is also clearly apparent that the internal synergism or amplification of antioxidation is not destroyed or impaired by conversion of the phenolic hydroxyl groups to addition products.

Catalytic Oxidation Test Procedure

The Catalytic Oxidation Test is to determine lubricants antioxidant properties. The test lubricant composition is subjected to a stream of air which is bubbled through the composition at a rate of 5 liters per hour at 325° F. for 40 hours. Present in the composition are metals commonly used as materials of engine construction, namely:

(a) 15.6 sq. in. of sand-blasted iron wire,
(b) 0.78 sq. in. polished copper wire,
(c) 0.87 sq. in. of polished aluminum wire, and
(d) 0.167 sq. in. of polished lead surface.

Inhibitors for oil are rated on the basis of prevention of oil deterioration as measured by the increase in acid formation or neutralization number (NN) and kinematic viscosity (KV) occasioned by the oxidation.

TABLE

| Catalytic Oxidation Test | | 325° F.; 4-HR., | | |
|---|---|---|---|---|
| Example No. | Conc., Wt. % | ΔNN | ΔKV, % | Pb Loss mg. |
| 1 | — | 17 | 334 | 66 |
| 2 | 2 | 5.7 | 72 | 0 |
|   | 1 | 6.2 | 75 | 0 |
|   | 0.5 | 6.9 | 79 | 0 |
| 3 | 2 | 0.96 | 29 | 0 |
|   | 1 | 1.0 | 21 | 0 |
|   | 0.5 | 1.8 | 24 | 0 |
| 4 | 2 | 0.74 | 29 | 0.2 |
|   | 1 | 1.8 | 26 | 0 |
|   | 0.5 | 4.4 | 42 | 1.8 |
| 5 | 2 | 1.6 | 35 | 0 |
|   | 1 | 1.0 | 41 | 1.6 |
|   | 0.5 | 3.1 | 42 | 3.2 |
| 6 | 2 | 1.4 | 32 | 2.3 |
|   | 1 | 3.1 | 40 | 1.6 |
|   | 0.5 | 4.6 | 46 | 2.2 |
| 7 | 2.0 | 2.3 | 41 | 0.4 |
|   | 1.0 | 4.9 | 57 | 0 |
|   | 0.5 | 6.8 | 90 | 3.5 |
| 8 | 2 | 1.8 | 35 | 0 |
|   | 1 | 4.1 | 47 | 0 |
|   | 0.5 | 6.5 | 76 | 1.3 |
| 9 | 1 | 0.31 | 27 | 0 |
|   | 0.5 | 0.84 | 20 | 0 |
| 10 | 1 | 0.70 | 23 | 0 |
|   | 0.5 | 1.3 | 22 | 0 |
| 11 | 2.0 | 1.95 | 34 | 2.9 |
|   | 1.0 | 3.0 | 36 | 3 |
|   | 0.5 | 4.4 | 40 | 1.7 |
| 12 | 1.0 | 0.46 | 22 | 0 |
|   | 0.5 | 0.71 | 10 | 0 |
| 13 | 1 | 0.10 | 22 | 0 |
|   | 0.5 | 0.80 | 19 | 0 |
| 14 | 1 | 0.63 | 9 | 0 |
|   | 0.5 | 0.86 | 10 | 0 |
| 15 | 2.0 | 3.9 | 18 | 3.1 |
|   | 1.0 | 6.4 | 74 | 0.8 |
|   | 0.5 | 8.1 | 111 | 4.5 |

It is understood that departures within the scope of the invention from the exemplary matter contained herein can be readily made.

I claim:
1. A compound or mixture of compounds prepared by reacting under suitable addition reaction conditions sulfurized phenols or oligomers thereof having the following structure:

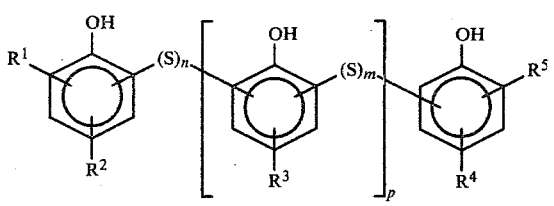

with at least one $C_1$–$C_{12}$ alkyl vinyl ether, whereby the final product is a compound or mixtures thereof having the structures:

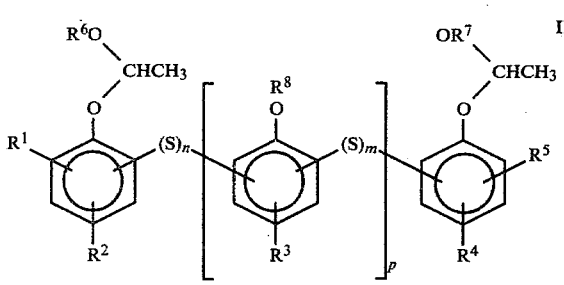

and

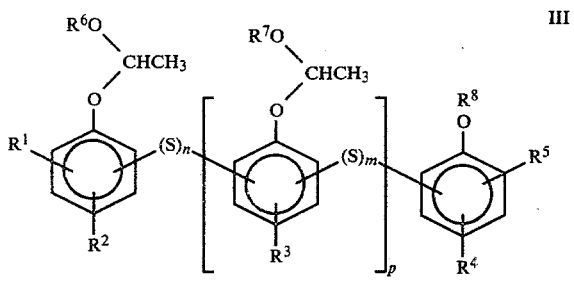

wherein $R^1$ and $R^5$ are hydrogen or alkyl groups having from 1 to about 16 carbon atoms in any isomeric structural arrangement, $R^1$ and $R^5$ are the same or different; $R^2$, $R^3$, and $R^4$ and hydrogen or an alkyl group having from 1 to about 18 carbon atoms in any isomeric structural arrangement, $R^2$, $R^3$ and $R^4$ are the same or different except that the total number of carbon atoms cannot be less than 4 if at least one of these substituent groups is hydrogen, $R^6$ and $R^7$ may be the same or different and are alkyl groups having from 1 to about 6 carbon atoms and $R^8$ is hydrogen or alkoxyalkyl having from 1 to about 6 carbon atoms; n and m are 1 to 4 and are the same or different, and p is 1 to 4 or zero.

2. The compound of claim 1 wherein the reaction is carried out using a molar ratio of alkyl vinyl ether to reactive hydroxyl groups in said sulfurized phenols of from about 0.25 to 10:1 at a temperature of from about 20° to 150° C.

3. The compound of claim 1 wherein the sulfurized phenol is selected from 2,2'-thiobis(alkylphenols); 2,2'-dithiobis(alkylphenols); oligomeric 2,2'-thiobis (alkylphenols), oligomeric 2,2'-dithiobis(alkylphenols) and mixtures thereof each containing from about 3 to 4 alkylphenol units wherein the alkyl moieties of said alkylphenol units contain from 1 to about 18 carbon atoms.

4. The compound of claim 3 wherein the alkyl moiety contains from about 4 to 12 carbon atoms.

5. The compound of claim 4 wherein the alkyl moiety is a 4-tert-octyl alkyl group.

6. The compound of claim 1 wherein 2,2'-thiobis(4-tert-butyl-6-methylphenol) is reacted with butyl vinyl ether and wherein said addition reaction is complete.

7. The compound of claim 6 wherein a molar ratio of 0.25 to 1 of vinyl ether to reactive hydroxyl groups is used and wherein said addition reaction is incomplete.

8. The compound of claim 5 wherein 2,2'-thiobis-(4-tert-octylphenol) is reacted with ethyl vinyl ether.

9. The compound of claim 5 wherein 2,2'-thiobis-(4-tert-octylphenol) is reacted with butyl vinyl ether and wherein said addition reaction is complete.

10. The compound of claim 5 wherein 2,2'-thiobis-(4-tert-octylphenol) is reacted with butyl vinyl ether and wherein said addition reaction is incomplete.

11. The compound of claim 5 wherein the sulfurized phenol derived from 2,2'-thiobis-(4-tert-octylphenol) is reacted with ethyl vinyl ether.

12. The compound of claim 5 wherein the sulfurized phenol derived from 2,2'-thiobis-(4-tert-octylphenol) is reacted with butyl vinyl ether.

13. The compound of claim 3 wherein the sulfurized phenol derived from 2-tert-butyl-4-methylphenol and p-cresol is reacted with butyl vinyl ether.

14. The compound of claim 3 wherein the sulfurized phenol derived from 4-tert-butyl-2-methylphenol and p-cresol is reacted with butyl vinyl ether.

15. The compound of claim 5 wherein 2,2'-thiobis-(4-tert-octylphenol) is sequentially reacted with ethyl vinyl ether and butyl vinyl ether.

16. An antioxidant lubricant composition comprising a minor effective amount of a compound prepared in accordance with claim 1 and a major amount of an oil of lubricating viscosity or grease prepared therefrom.

17. The composition of claim 16 wherein the preparation is carried out using a molar ratio of alkyl vinyl ether to reactive hydroxyl groups in said sulfurized phenols of from about 0.25 to 10:1 at a temperature of from about 20° to 150° C.

18. The composition of claim 16 wherein the sulfurized phenol is selected from 2,2'-thiobis(alkylphenols); 2,2'-dithiobis(alkylphenols); oligomeric 2,2'-thiobis(alkylphenols), oligomeric 2,2'-dithiobis(alkylphenols) and mixtures thereof containing from 3 to 4 alkylphenol units wherein the alkyl moieties contain from 1 to about 20 carbon atoms.

19. The composition of claim 16 wherein the alkyl moiety contains from about 4 to 12 carbon atoms.

20. The composition of claim 19 wherein the alkyl moiety is a p-tert-octyl alkyl group.

21. The composition of claim 16 wherein 2,2'-thiobis(4-tert-butyl-6-methylphenol) is reacted with butyl vinyl ether and wherein said addition reaction is complete.

22. The composition of claim 21 wherein a molar ratio of 0.25 to 1 of vinyl ether to reactive hydroxyl groups is used and wherein said addition reaction is incomplete.

23. The composition of claim 18 wherein 2,2'-thiobis-(4-tert-octylphenol) is reacted with butyl vinyl ether and wherein said addition reaction is complete.

24. The composition of claim 18 wherein 2,2'-thiobis-(4-tert-octylphenol) is reacted with ethyl vinyl ether.

25. The composition of claim 18 wherein 2,2'-thiobis-(4-tert-octylphenol) is reacted with butyl vinyl ether.

26. The composition of claim 20 wherein sulfurized 4-tert-octylphenol is reacted with ethyl vinyl ether.

27. The composition of claim 20 wherein sulfurized 4-tert-octylphenol is reacted with butyl vinyl ether.

28. The composition of claim 16 wherein a mixture of sulfurized 2-tert-butyl-4-methylphenol and p-cresol is reacted with butyl vinyl ether.

29. The composition of claim 16 wherein a mixture of sulfurized 4-tert-butyl-2-methylphenol and p-cresol is reacted with butyl vinyl ether.

30. The composition of claim 16 wherein 2,2'-thiobis-(4-tert-octylphenol) is sequentially reacted with ethyl vinyl ether and butyl vinyl ether.

* * * * *